(12) United States Patent
Kvaløy et al.

(10) Patent No.: US 12,714,604 B2
(45) Date of Patent: Aug. 25, 2026

(54) HEARING PROTECTION

(71) Applicant: MINUENDO AS, Oslo (NO)

(72) Inventors: Olav Kvaløy, Oslo (NO); Tom Trones, Oslo (NO)

(73) Assignee: MINUENDO AS, Oslo (NO)

( * ) Notice: Subject to any disclaimer, the term of this patent is extended or adjusted under 35 U.S.C. 154(b) by 179 days.

(21) Appl. No.: 18/576,950

(22) PCT Filed: Jul. 6, 2022

(86) PCT No.: PCT/GB2022/051730
§ 371 (c)(1),
(2) Date: Jan. 5, 2024

(87) PCT Pub. No.: WO2023/281255
PCT Pub. Date: Jan. 12, 2023

(65) Prior Publication Data

US 2024/0245554 A1 Jul. 25, 2024

(30) Foreign Application Priority Data

Jul. 6, 2021 (GB) ..................................... 2109716

(51) Int. Cl.
*A61F 11/14* (2006.01)
*A61F 11/08* (2006.01)

(52) U.S. Cl.
CPC ............ *A61F 11/145* (2022.01); *A61F 11/08* (2013.01)

(58) Field of Classification Search
CPC ............................... A61F 11/145; A61F 11/08
See application file for complete search history.

(56) References Cited

U.S. PATENT DOCUMENTS

2004/0190729 A1* 9/2004 Yonovitz .................. G01H 3/14 381/72
2012/0029383 A1* 2/2012 Henriksen ............... A61F 11/08 600/559

(Continued)

FOREIGN PATENT DOCUMENTS

WO WO-2014060711 A1 * 4/2014 ............ A61F 11/145
WO WO 2017/027186 A1 2/2017
WO WO 2021/074651 A1 4/2021

OTHER PUBLICATIONS

International Search Report and Written Opinion of PCT/GB2022/051730, mailed Oct. 10, 2022, 13 pages.

(Continued)

*Primary Examiner* — Olisa Anwah
(74) *Attorney, Agent, or Firm* — Heslin Rothenberg Farley & Mesiti P.C.; George S. Blasiak, Esq.

(57) ABSTRACT

A hearing protection system comprises a hearing protection device adapted for placement over or insertion into a user's ear. The hearing protection device comprises a first microphone arranged to determine an internal sound level characteristic within the user's ear canal. The hearing protection system further comprises a second microphone arranged to determine an ambient sound level characteristic. The system is arranged to compare the internal and ambient sound level characteristics to determine a difference metric therebetween and to generate an indication if the difference metric is greater than a difference threshold and the internal sound level characteristic is lower than an internal sound threshold.

16 Claims, 6 Drawing Sheets

(56) References Cited

U.S. PATENT DOCUMENTS

Figure 1:
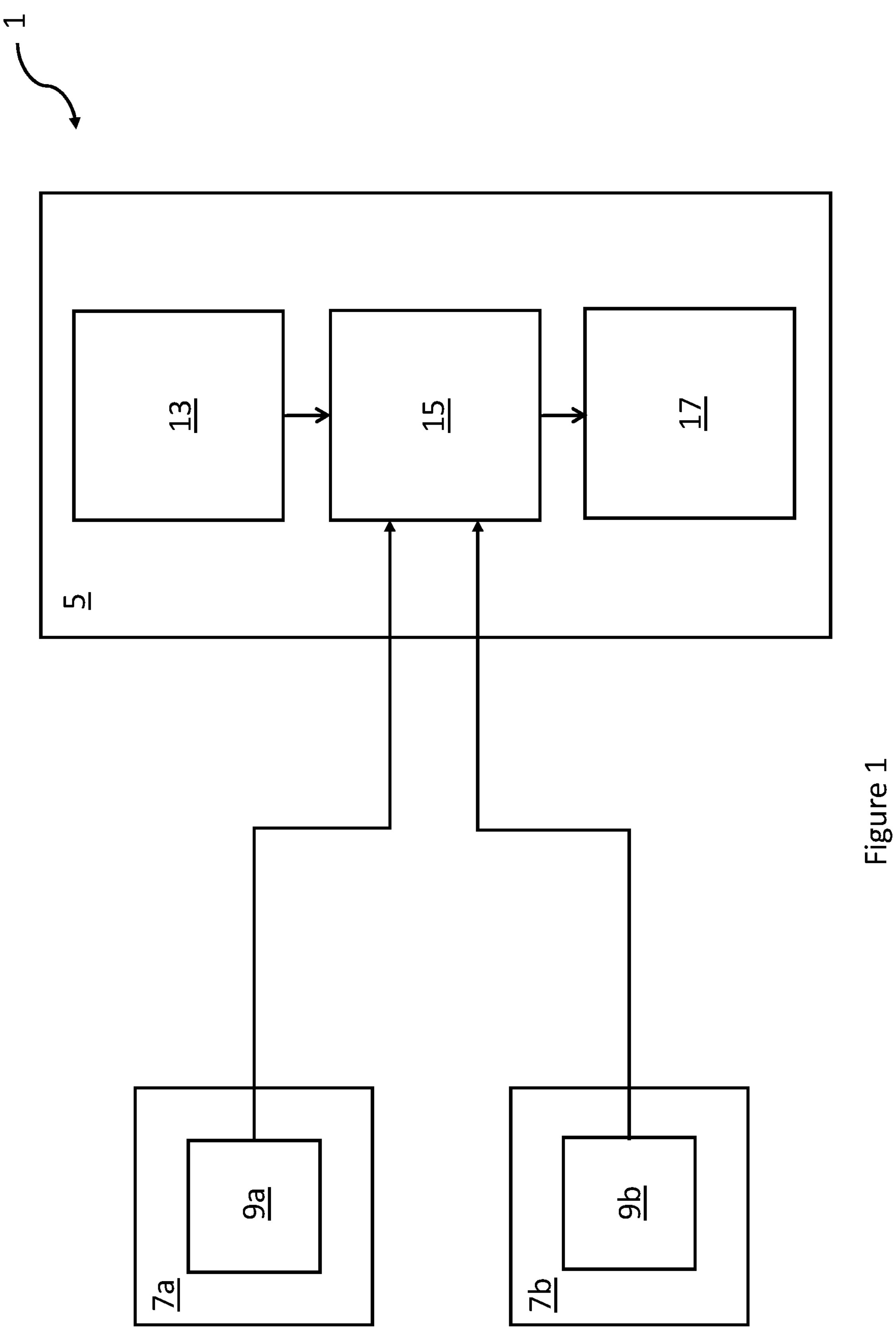

2014/0294191 A1* 10/2014 Parkins .................. A61F 11/06
381/72
2015/0010158 A1 1/2015 Broadley et al.

OTHER PUBLICATIONS

Search Report from the Intellectual Property Office for United Kingdom Application No. 2109716.7, mailed on Apr. 7, 2022, 4 pages.

* cited by examiner

HEARING PROTECTION

CROSS REFERENCE TO RELATED APPLICATIONS

This application is a national stage filing under section 371 of International Application No. PCT/GB2022/051730 filed on Jul. 6, 2022, and published on Jan. 12, 2023, as WO 2023/281255 and claims priority to United Kingdom Application No. 2109716.7 filed on Jul. 6, 2021. The entire contents of WO 2023/281255 are hereby incorporated herein by reference.

The present invention relates to hearing protection, and more particularly to hearing protection systems in which a user has some control over the level of protection provided.

Hearing protection is worn by users in a wide variety of scenarios where high levels of sound have the potential to damage ears and/or hearing. Hearing protection can include in-ear devices such as deformable plugs, over-ear devices such as ear muffs secured with a head band, or a combination of both. For example, it is common for workers in high noise environments to use double-protection using in-ear plugs and over-ear muffs at the same time.

In many situations the level of sound varies over time and between different areas within a workplace and it can be difficult for an individual to remain aware of these changes.

According to a first aspect of the invention, there is provided a hearing protection system comprising a hearing protection device adapted for placement over or insertion into a user's ear, said hearing protection device comprising a first microphone arranged to determine an internal sound level characteristic within the user's ear canal, said hearing protection system further comprising:

- a second microphone arranged to determine an ambient sound level characteristic, the system being arranged to compare said internal and ambient sound level characteristics to determine a difference metric therebetween and to generate an indication if said difference metric is greater than a difference threshold and said internal sound level characteristic is lower than an internal sound threshold.

According to a second aspect of the invention, there is provided a method of determining whether a user's hearing is overprotected, comprising: determining an internal sound level characteristic within the user's ear canal; determining an ambient sound level characteristic; comparing the internal and ambient sound level characteristics to determine a difference metric therebetween; comparing the difference metric with a difference threshold; comparing the internal sound level characteristic with an internal sound threshold; and generating an indication if said difference metric is greater than the difference threshold and said internal sound level characteristic is lower than the internal sound threshold.

Thus it will be seen by those skilled in the art that in accordance with the invention, a situation where a user's hearing is being overprotected can be identified, and the user can thus be notified such that they may take steps to reduce the level of hearing protection they are wearing. The inventors have realised that commonly used hearing protection devices (HPD), both earplugs and earmuffs, may provide attenuation in the range of 30 to 40 dB if worn correctly. In very noisy situations, eg. ambient noise level more than 110 dBA, this is needed, but when the noise levels are in the medium to lower range, this high attenuation is not needed for hearing protection. In addition, oral communication is almost impossible with this high level of attenuation. Since communication is often necessary the user will need to remove the HPD to be able to communicate. This situation is called overprotection because the level of attenuation is too high due to the moderate ambient noise level and the need for communication.

Overprotection may occur, for example, when a user is wearing both an in-ear hearing protection device, such as earplugs, and an over-ear hearing protection device such as ear muffs. Where a user's hearing is overprotected, the level of sound attenuation may be too high for the level of ambient sound that is present. This overprotection can make verbal communication with the user difficult as mentioned above, and the risk of accidents may be increased when a user is audibly isolated from their environment since their situational awareness may be significantly affected.

The indication could be provided whenever the conditions set out above are met. However, in a set of embodiments, the indication is not generated if the ambient sound level characteristic is greater than an ambient sound threshold. Such an ambient sound threshold condition may help to ensure that it is not indicated to a user that their hearing is overprotected if the ambient sound level is too high. Such a condition would not normally be expected to arise but this feature may be advantageous in helping to avoid a situation whereby a user removes their hearing protection device, or reduces their level of hearing protection in response to an indication, exposing their hearing to the high sound level.

The hearing protection device may be adapted for placement over a user's ear. However, in a set of embodiments, the hearing protection device is adapted for insertion into the user's ear canal.

The second microphone may be provided on the hearing protection device, but in a set of embodiments, the second microphone is provided separately from the hearing protection device. Providing the second microphone separately from the hearing protection device may allow for a better determination of the ambient sound level, as compared with the internal sound level. It may also reduce the weight of the hearing protection device and reduce the need for miniaturisation of the second microphone which may in turn reduce the cost of the device. Further, providing the second microphone separately from the hearing protection device and away from the user's ear may allow the system to be more versatile. For example, in embodiments where the hearing protection device is adapted to be inserted into a user's ear canal, having the second microphone away from the device prevents its operation being hampered should the user wear a separate over-ear hearing protection device, such as a pair of ear muffs.

The second microphone may be provided by a third party device, such as a smartphone. However, in a set of embodiments, the second microphone is provided on a collar or other support member adapted to be worn away from the user's ear.

The indication could be provided whenever the conditions set out above are met. However, in a set of embodiments, the hearing protection system of the first aspect, and/or the method of the second aspect determines whether the user is properly wearing the hearing protection device and does not generate the indication if it is determined that the user is not properly wearing the hearing protection device. Determining whether the user is properly wearing the hearing protection device may comprise directly comparing the sound levels from the first microphone and second microphone, and/or generating a test sound to be detected by the microphones.

Such methods are described in more detail in WO2021/074651, the contents of which are hereby incorporated by reference.

The indicator may be an audio device, a vibrating element or any other element suitable for giving an indication to the user. However, in a set of embodiments, the indicator is a light emitting element. In a particular set of embodiments, the indicator is a light emitting diode (LED). A visual indicator, such as a light emitting element may be advantageous since audible indications or vibratory indications may be missed in the high noise environments where hearing protection is likely to be used.

The value of the internal sound threshold may be between 60 dB (decibels) and 80 dB. In particular, it may be 70 dB.

The value of the difference threshold may be between 15 dB and 32 dB. In particular, it may be 28 dB.

The value of the ambient sound threshold may be between 90 dB and 110 dB. In particular, it may be 100 dB.

In embodiments, the system may comprise only the first and second microphones, however, in a set of embodiments, the system comprises a third microphone arranged to determine an internal sound level within the user's ear canal. For example, the first microphone may be arranged to determine an internal sound level within the user's left ear canal, and the third microphone may be arranged to determine an internal sound level within the user's right ear canal, or vice versa. In such embodiments, it may be that the system is arranged to determine a first difference metric between the internal sound level characteristic determined by the first microphone, and the ambient sound level characteristic determined by the second microphone, and further to determine a second difference metric between the internal sound level characteristic determined by the third microphone, and the ambient sound level characteristic determined by the second microphone.

In embodiments where a third microphone is provided, the method of the second aspect may further comprise determining a second internal sound level within the user's ear canal, and determining a second difference metric between the internal sound level characteristic determined by the third microphone, and the ambient sound level characteristic. The method may then generate an indication only when both the first and second difference metrics are greater than a difference threshold, and when both the first and second internal sound level characteristics are lower than an internal sound threshold.

In a set of embodiments an indication is only generated when both the first and second difference metrics are greater than the difference threshold, and when both the first and second internal sound level characteristics are lower than the internal sound threshold. Such embodiments may be advantageous in ensuring that indications are not wrongly given when sound is highly directional. For example, in an embodiment without a third microphone, if the first microphone was monitoring an internal sound level characteristic in a user's left ear, but a sound source was much closer to the user's right ear, then the system may give an overprotection indication as a result of the internal sound level characteristic in the user's left ear, but removing hearing protection may still expose the user's right ear to potentially harmful sound levels. Further, such embodiments may be advantageous in helping the system to continue to give accurate indications even if one side of the hearing protection device is not inserted or placed over the user's ear, for example if a user has removed one side to have a conversation.

Embodiments of the invention have been discussed in relation to a user's ear, and ear canal. It will be understood by the person skilled in the art that such references are equally applicable to both of a user's ears, and that the hearing protection device of the invention may be adapted for placement over or insertion into both of a user's ears.

The features described above in relation to different aspects and embodiments of the present invention may be combined in various combinations. It will be understood that the combination of features in the following description and drawings are intended to be illustrative, and are non-limiting.

Figure 2:
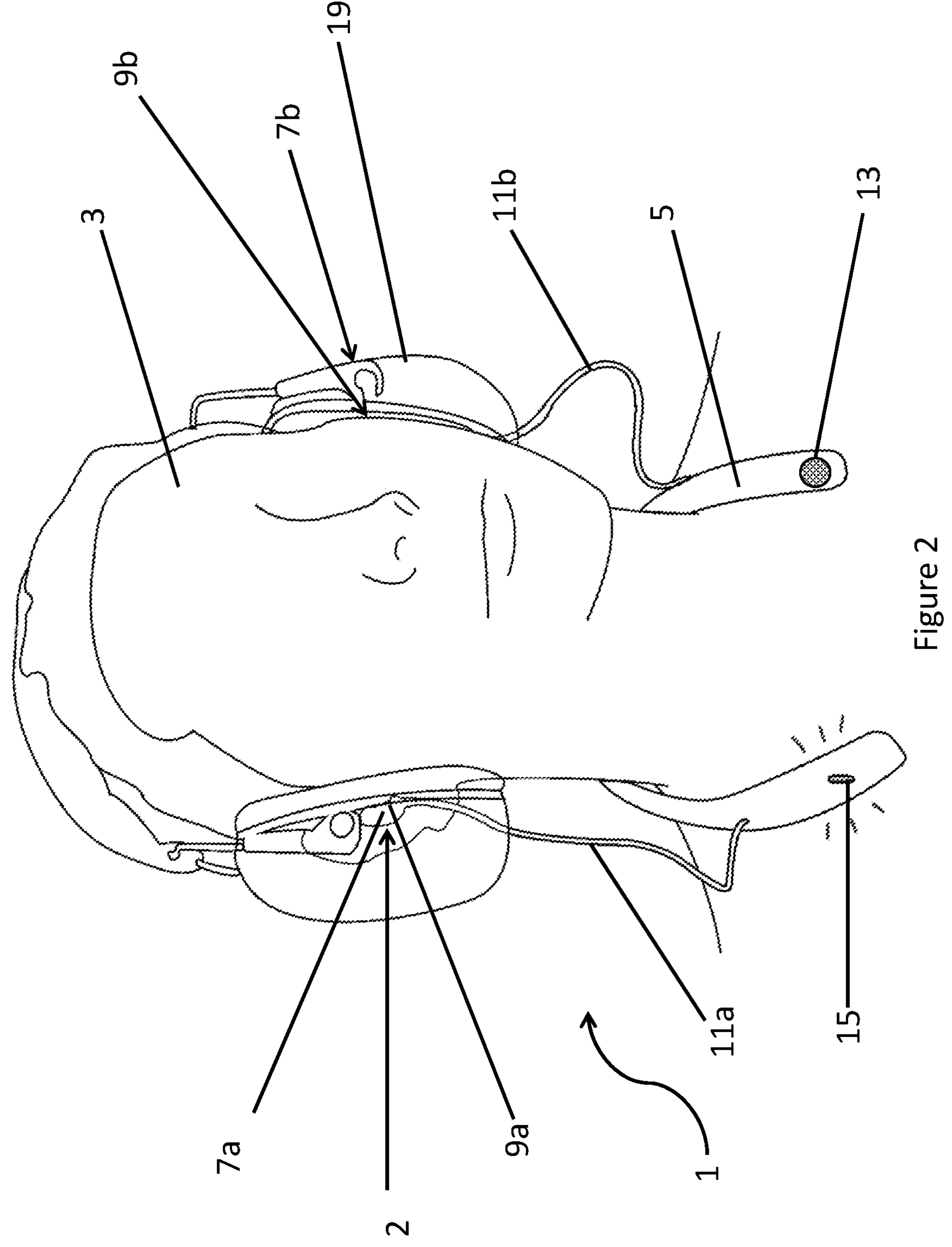
Figure 3:
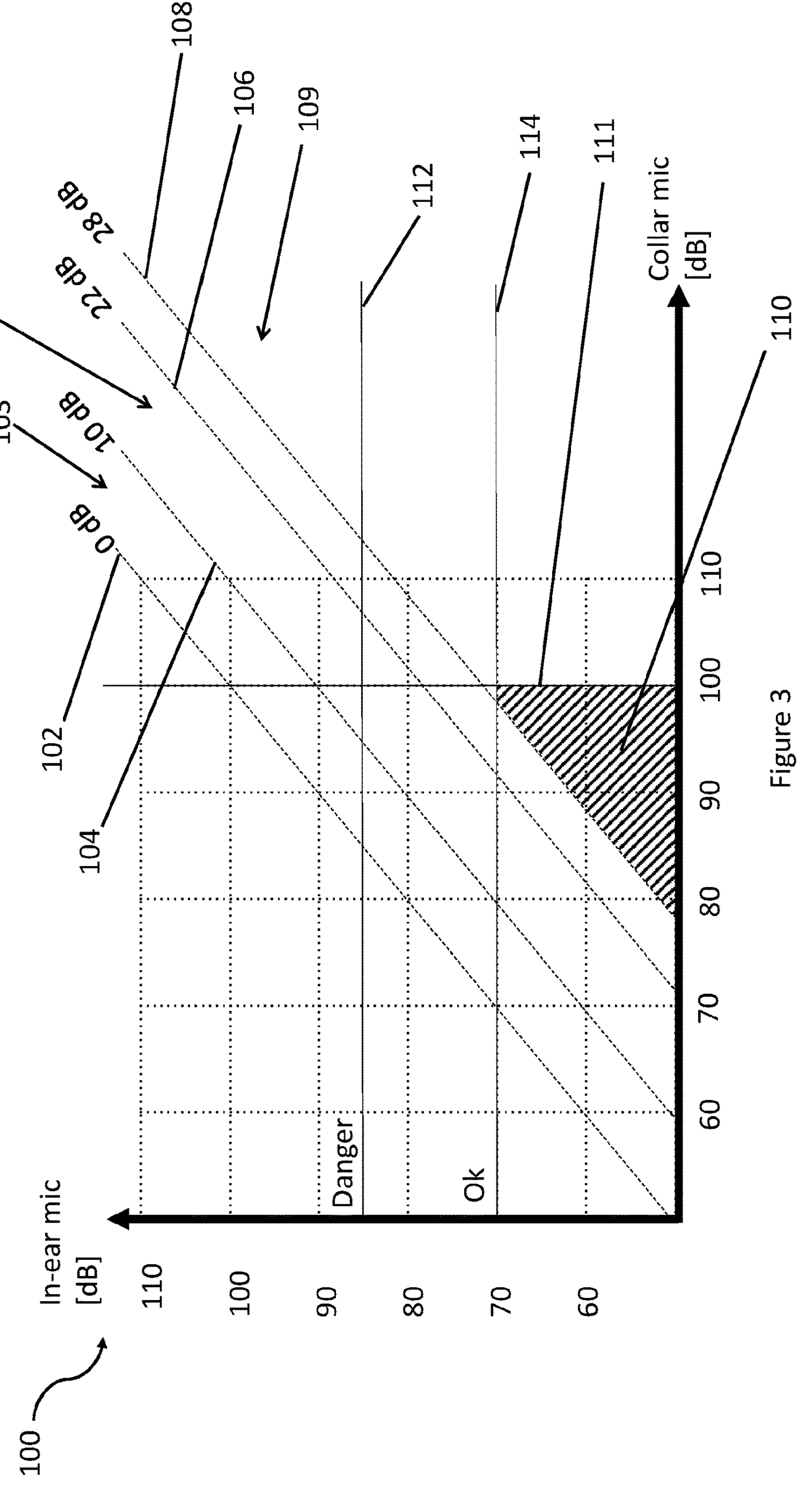
Figure 4:
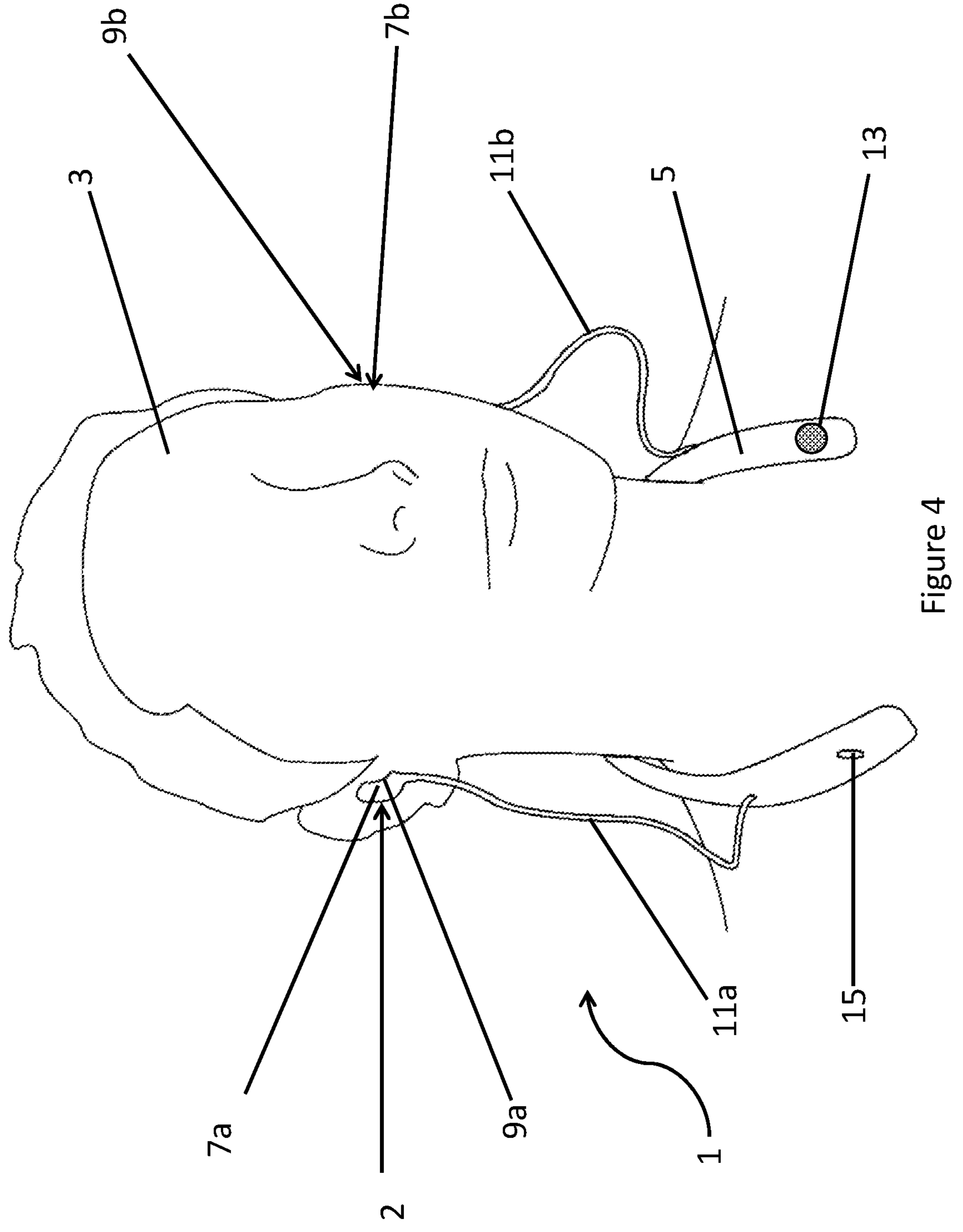
Figure 5A:
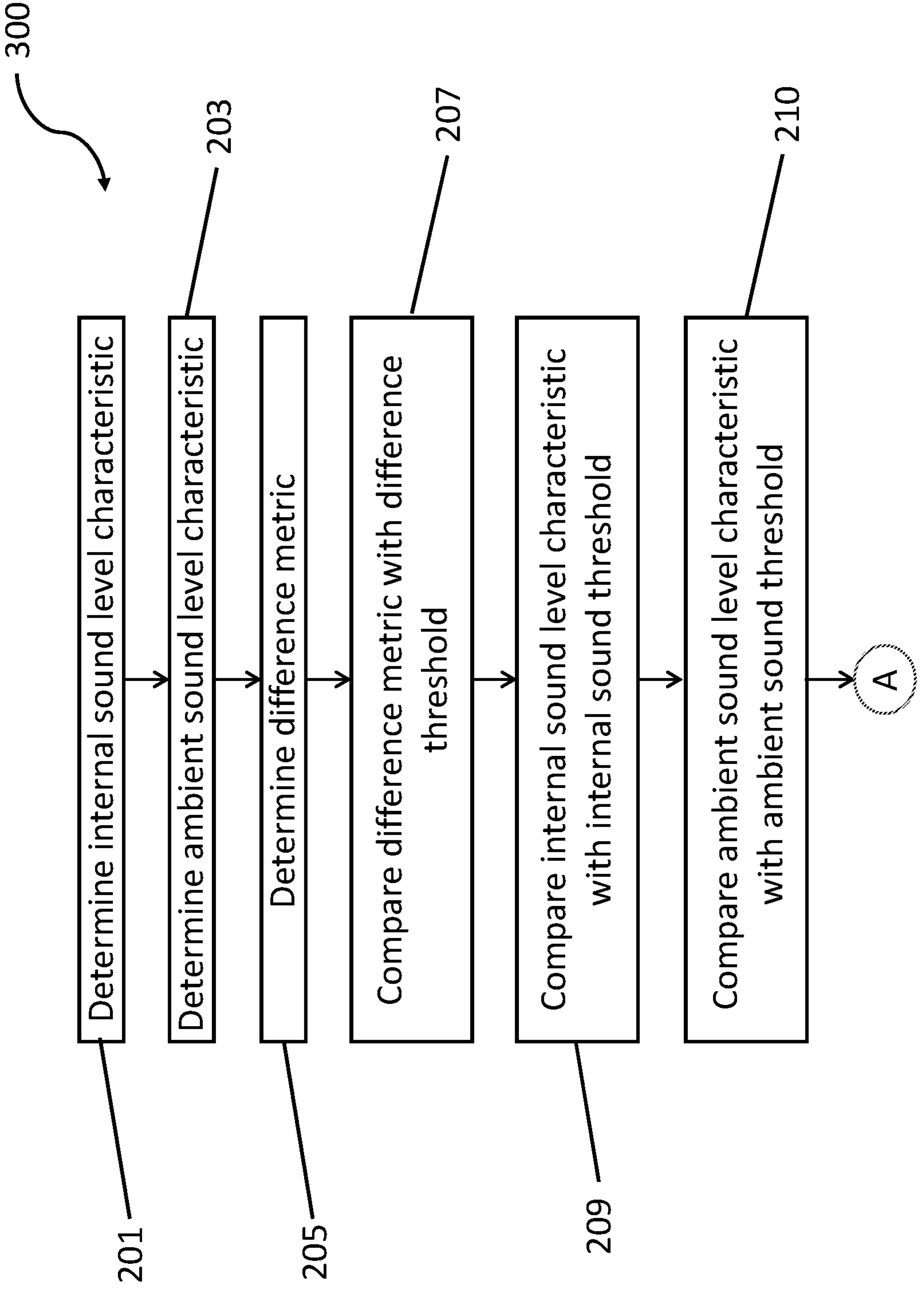
Figure 5B:
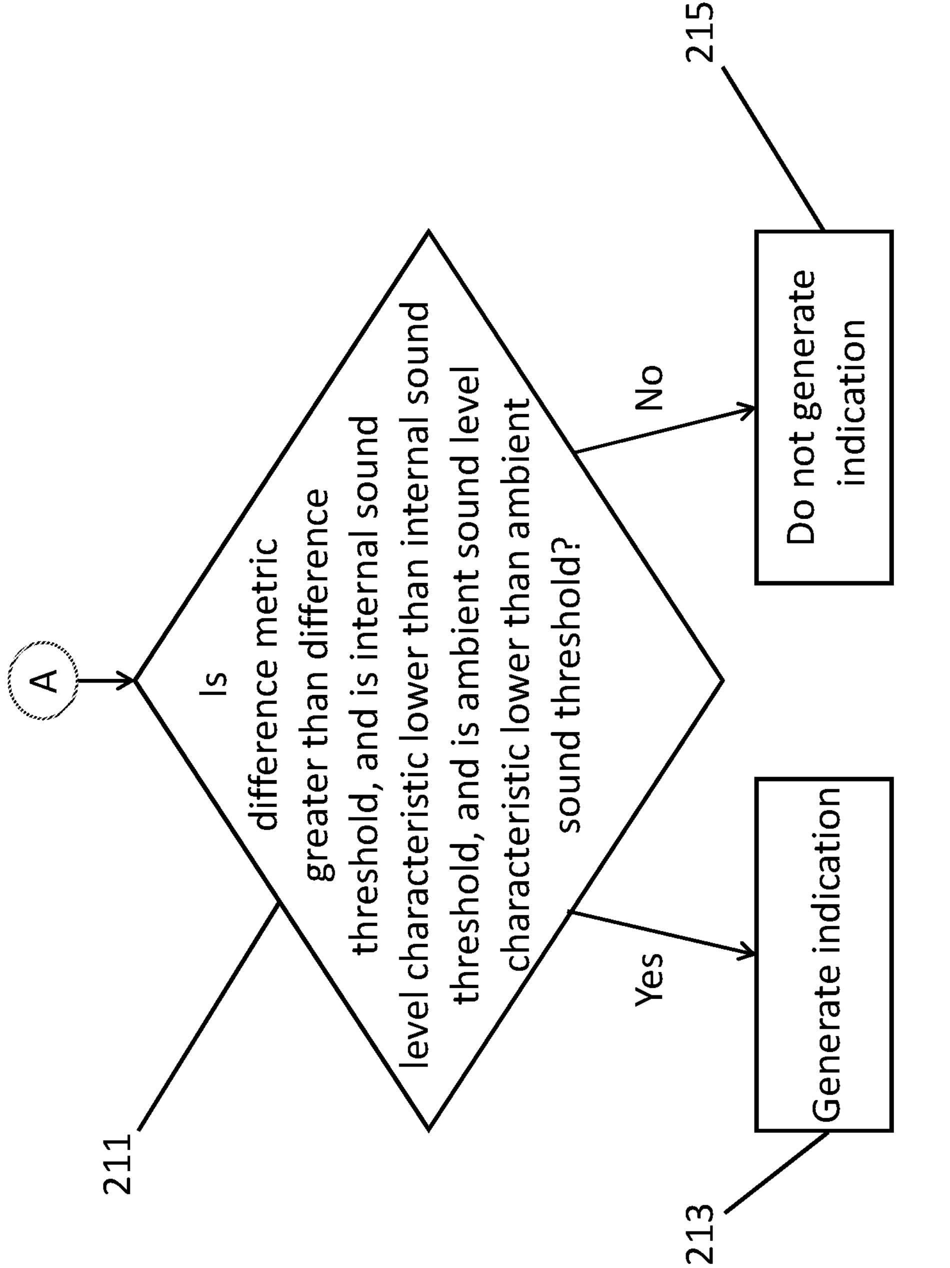

An embodiment of the invention will now be described, by way of example only, with reference to the accompanying drawings in which:

FIG. 1 is a block diagram of a hearing protection system in accordance with an embodiment of the present invention;

FIG. 2 schematically shows a hearing protection system in accordance with an embodiment of the present invention in use on a user in an overprotected state;

FIG. 3 is a graph comparing in-ear sound levels to ambient sound levels;

FIG. 4 schematically shows the hearing protection system of FIG. 2 in use on a user in a non-overprotected state;

FIGS. 5*a* and 5*b* are a flow diagram showing the steps of a method in accordance with an embodiment of the present invention.

FIG. 1 is a block diagram of a hearing protection system 1 which includes a first hearing protection device 7*a*—e.g. in the form of an ear-plug configured to be inserted into a user's left ear canal, having a first microphone 9*a* arranged to determine an internal sound characteristic such as sound pressure level within the left ear canal of the user. The hearing protection system 1 further includes a support member 5, e.g. in the form of a neck collar, which houses a second microphone 13 arranged to determine an ambient sound level characteristic, a processor 17, and an LED indicator 15. The system also includes a second hearing protection device 7*b*—e.g. in the form of an ear-plug configured to be inserted into the user's right ear canal and having a third microphone 9*b* arranged to determine an internal sound characteristic such as sound pressure level within the right ear canal of the user. The three microphones 9*a*, 9*b*, 13 are connected to the processor 17, e.g. by means of wires and the processor 17 is also connected to the LED indicator 15.

FIG. 2 shows the hearing protection system 1 in situ on a user 3. As mentioned above, the first microphone 9*a* determines an internal sound pressure level within the ear canal of the user 3 when the earplug 7*a* is inserted into the ear canal. The earplugs 7*a*, 7*b* are connected to the collar 5 by respective wires 11*a*, 11*b* to provide the aforementioned connections between the microphones 9*a*, 9*b* and the processor 17. As may be seen, the user 3 is also wearing a standard pair of over-ear defenders or muffs 19.

Operation of the system will now be described with reference to FIG. 3 which shows a graph 100 comparing in-ear (internal) sound levels from one of the hearing protection devices 7*a* to ambient sound levels. The processor 17 receives a signal representing the determined internal sound pressure level from the first microphone 9*a*, and the determined ambient sound pressure level from the second microphone 13. The processor 17 compares the determined internal sound pressure level and the ambient sound pressure level to determine a difference metric therebetween, The difference metric is calculated by subtracting the value measured by the in-ear microphone (first microphone 7*a*) from the value measured by the collar microphone (second microphone 13).

Line 102 shows a difference metric of 0 dB, typically when no hearing protection is used. Line 104 shows a difference metric 10 dB, line 106 shows a difference metric of 22 dB, and line 108 shows a difference metric of 28 dB which represents a difference threshold value. The region 103 between lines 102 and 104 represents the difference metric values associated with poorly fitted hearing protection. The region 105 between lines 104 and 106 represents the difference metric values associated with medium fitted to well fitted hearing protection. The region 109 to the right of difference threshold value line 108 represents the difference metric values associated with double hearing protection devices, i.e. when the ear-muffs 19 are being worn too which may, in some circumstances, provide excessive protection.

Looking at the horizontal axis, representing the ambient sound pressure level measured by the microphone 13 on the collar 5, the ambient sound pressure level threshold 111 can be seen.

Now looking at the vertical axis, line 112 is drawn at an in-ear sound level of 85 dB. It is accepted that SPLs above this can be dangerous at which damage to hearing can occur. Line 114 is drawn at an in-ear sound level of 70 dB. This is deemed to be far enough below the dangerous 85 dB level to be an acceptable in-ear noise level, thus, in the illustrated embodiment, the internal sound pressure level threshold 114 is set at 70 dB.

The shaded region of the graph 110 is defined as the 'overprotection' region 110. This is the region in which the difference metric is above the difference threshold 108, the internal sound pressure level is below the threshold value 114, and the ambient sound pressure level is below the ambient threshold value 111.

When the processor 17 determines that the conditions are in the overprotection region 110, a signal is sent to the indicator 15 to illuminate the LED, informing the user 3 that their hearing is being over-protected.

In the situation of FIG. 2, the user 3 is wearing the hearing protection devices 7*a*, 7*b* as well as an over-ear hearing protection device 19. The hearing protection system 1 has determined that the user's hearing is being overprotected, and so the LED 15 is illuminated.

FIG. 4 shows the hearing protection system 1 of FIG. 2 with the over-ear hearing protection device 19 removed. The hearing protection system 1 has determined that the user's hearing is not overprotected, and as such, the LED 15 is not illuminated.

FIGS. 5 and 4*b* are a flow diagram illustrating a method 200 in accordance with the invention. The method of FIGS. 5*a* and 5*b* is carried out using the hearing protection system 1 of FIG. 1, FIG. 2, and FIG. 4. At step 201, the internal sound level characteristic (such as sound pressure level) is determined by the first microphone 9*a*. At step 203, the ambient sound level characteristic (sound pressure level) is determined by the second microphone 13. At step 205, the internal sound level characteristic is subtracted from the ambient sound level characteristic by the processor 17 to determine the difference metric between the two. At step 207, the difference metric determined by step 205 is compared with the difference threshold at the processor 17. At step 209, the internal sound level characteristic is compared with the internal sound threshold at the processor 17.

The method 200 further incudes step 210 at which the ambient sound level characteristic is compared with an ambient sound threshold at the processor 17. Decision step 211 of method 200 takes the results from the comparison of step 207, the comparison of step 209, and the comparison of step 210. If the difference metric is greater than the difference threshold, and the internal sound level characteristic is lower than the internal sound threshold, and the ambient sound level characteristic is lower than the ambient sound threshold, then the processor 17 sends a signal to the indicator 15, the method proceeds to step 213, and an indication is generated at the indicator 15. If the difference metric is lower than the difference threshold, and/or the internal sound level characteristic is greater than the internal sound threshold, and/or the ambient sound level characteristic is greater than the ambient sound threshold, then the processor 17 does not send a signal to the indicator 15, the method proceeds to step 215, and an indication is not generated.

In the illustrated embodiment, earplug 7*b* comprises a third microphone 9*b*, but the internal sound pressure level measured by the third microphone 9*b* is not used in the method 200 of FIGS. 5*a* and 5*b*. It will be understood that either or both of the internal sound measurements from the first microphone 9*a* and the third microphone 9*b* can be used respectively in the determination step 201, the determination step 203, and the comparison step 209. For example, the internal sound level measured by the first microphone 9*a* may be replaced with the internal sound level measured by the third microphone 9*b* in steps 201, 203, and 209, or, where both internal sound measurements are used, a difference metric may be determined for each earplug 7*a*, 7*b*, and an indication may not be generated unless both of the difference metrics are greater than the difference threshold, both of the internal sound characteristics are lower than the internal sound threshold, and the ambient sound level characteristic is lower than the ambient sound threshold. In other words, an indication is only given if overprotection is determined for both ears.

In the illustrated embodiment, the difference threshold is set at 28 dB, the internal sound threshold is set at 70 dB, and the ambient sound threshold is set at 100 dB, but it will be understood that these values may be altered to suit the circumstances.

In the illustrated embodiment, the threshold values have been set at levels appropriate for the average adult's hearing. It is envisaged that these threshold values may be changed for different users and/or different environments. Each threshold value may be dynamically adjusted based on factors such as user vulnerability/sensitivity, hearing loss, individual preferences, previous high noise exposure, Left/Right differences, or the number of peaks vs stationary noise in the ambient sound.

In the illustrated embodiment, the indication is given by means of a visual cue, namely the illumination of an LED. It is envisaged that any suitable indication may be given by any suitable indication means. For example, the indication may be given by a vibrating element, or by an audible cue played into the user's ear. The skilled person will readily understand how to implement various indication means.

In the illustrated embodiment, the hearing protection devices 7*a*, 7*b* are connected to the support member 5 by means of wires 11*a*, 11*b*. It is envisaged that the hearing protection devices 7*a*, 7*b* may be wireless, and may communicate with the support member 5 by any suitable means, such as, for example, via Bluetooth, WiFi, or Infrared.

Whilst the illustrated embodiment has a single processor 17, it is envisaged that the hearing protection system 1 of the invention could comprise a plurality of processors, and the processing tasks discussed above could be performed by one or more processors.

It is envisaged that the processor 17, and second microphone 13 may be provided by a third party device, such as, for example, a smart phone or smart watch. In such embodiments, the hearing protection devices 7*a*, 7*b* may interact with the third party device in any known manner, and an application may be installed on the third party device to configure the third party device for use in the hearing protection system 1.

The invention claimed is:

1. A hearing protection system comprising:

a first hearing protection device adapted for placement over or insertion into a user's ear canal, said hearing protection device comprising a first microphone arranged to determine an internal sound level characteristic within the user's ear canal, a second hearing protection device adapted for placement over the first hearing protection device; and a second microphone arranged to determine an ambient sound level characteristic, the system being arranged to:

compare said internal and ambient sound level characteristics to determine a difference metric therebetween;

determine that the second hearing protection device is placed over the first hearing protection device if said difference metric is greater than a difference threshold; and generate an indication that the user's hearing is overprotected if the second hearing protection device is placed over the first hearing protection device and said internal sound level characteristic is lower than an internal sound threshold.

2. The hearing protection system as claimed in claim 1, arranged so as not to generate said indication if said ambient sound level characteristic is greater than an ambient sound threshold.

3. The hearing protection system as claimed in claim 2, wherein said ambient sound threshold is between 90 dB and 110 dB.

4. The hearing protection system as claimed in claim 1, wherein said hearing protection device is adapted for insertion into said user's ear canal.

5. The hearing protection system as claimed in claim 1, wherein said second microphone is provided separately from said first hearing protection device.

6. The hearing protection system as claimed in claim 4, wherein said second microphone is provided on a collar or other support member adapted to be worn away from the user's ear.

7. The hearing protection system as claimed in claim 1, arranged to determine whether said user is properly wearing said first hearing protection device and not to generate said indication if it is determined that the user is not properly wearing said first hearing protection device.

8. The hearing protection system as claimed in claim 1, wherein the indication means is a light emitting element.

9. The hearing protection system as claimed in claim 1, wherein said internal sound threshold is between 60 dB and 80 dB.

10. The hearing protection system as claimed in claim 1, wherein said difference threshold is between 15 dB and 32 dB.

11. A method of determining whether a user's hearing is overprotected, comprising:

determining an internal sound level characteristic within an ear canal of the user;

determining an ambient sound level characteristic;

comparing the internal and ambient sound level characteristics to determine a difference metric therebetween;

comparing the difference metric with a difference threshold;

determining that a second hearing protection device is placed over a first hearing protection device adapted for placement over or insertion into the ear canal of the user if said difference metric is greater than the difference threshold;

comparing the internal sound level characteristic with an internal sound threshold; and generating an indication that the user's hearing is overprotected if the second hearing protection device is placed over the first hearing protection device and said internal sound level characteristic is lower than the internal sound threshold.

12. The method as claimed in claim 11, further comprising comparing the ambient sound level characteristic with an ambient sound threshold, and not generating said indication if said ambient sound level characteristic is greater than the ambient sound threshold.

13. The method as claimed in claim 12, wherein said ambient sound threshold is between 90 dB and 110 dB.

14. The method as claimed in claim 11, further comprising determining whether said user is properly wearing said first hearing protection device and not generating said indication if it is determined that the user is not properly wearing said hearing protection device.

15. The method as claimed in claim 11, wherein said internal sound threshold is between 60 dB and 80 dB.

16. The method as claimed in claim 11, wherein said difference threshold is between 15 dB and 32 dB.

* * * * *